(12) United States Patent
Chen et al.

(10) Patent No.: US 7,469,488 B2
(45) Date of Patent: *Dec. 30, 2008

(54) CONTROL OF PROCESS HUMIDITY TO PRODUCE LARGE, POROUS PARTICLES

(75) Inventors: Donghao Chen, Lexington, MA (US); Richard P. Batycky, Newton, MA (US); Lloyd Johnston, Belmont, MA (US); Jeffrey Mintzes, Brighton, MA (US)

(73) Assignees: Alkermes, Inc., Cambridge, MA (US); The Penn State Research Foundation, University Park, PA (US)

( * ) Notice: Subject to any disclaimer, the term of this patent is extended or adjusted under 35 U.S.C. 154(b) by 679 days.

This patent is subject to a terminal disclaimer.

(21) Appl. No.: 10/977,088

(22) Filed: Oct. 29, 2004

(65) Prior Publication Data
US 2005/0058607 A1    Mar. 17, 2005

Related U.S. Application Data

(62) Division of application No. 09/837,620, filed on Apr. 18, 2001, now Pat. No. 6,848,197.

(51) Int. Cl.
*E02F 5/10* (2006.01)
*A01N 25/02* (2006.01)
*A61K 9/14* (2006.01)
*A05D 7/00* (2006.01)

(52) U.S. Cl. .............. 34/373; 424/43; 424/46; 424/489; 514/951; 34/372; 427/213

(58) Field of Classification Search ............ 34/372, 34/373; 427/213; 514/951; 424/422, 434, 424/489, 490, 43, 46
See application file for complete search history.

(56) References Cited

U.S. PATENT DOCUMENTS

| 3,495,458 A | 2/1970 | Christensen |
| 4,422,900 A | 12/1983 | Bordelon et al. |

(Continued)

FOREIGN PATENT DOCUMENTS

WO    WO 91/16882    11/1991

(Continued)

OTHER PUBLICATIONS

Mintzes, Jeffrey, Spray Drying of Large porous Particles For Aerosol Drug Delivery To The Lung,, pp. 1-37.*

(Continued)

*Primary Examiner*—Sharmila Landau
(74) *Attorney, Agent, or Firm*—Elmore Patent Law Group; Carolyn S. Elmore; Darlene A. Vanstone

(57) ABSTRACT

Spray dried particles having specified aerodynamic characteristics are produced by atomizing a liquid feed and contacting the liquid feed with a drying gas, such as, for example, air or nitrogen. The humidity of the drying gas is controlled to a value, expressed, for instance, as dew point, which is known to produce particles having a specified tap density or aerodynamic diameter. Particles having a volume median geometric diameter greater than about 5 microns and a tap density less than about 0.4 g/cm$^3$ are preferred.

13 Claims, 4 Drawing Sheets

U.S. PATENT DOCUMENTS

| | | | |
|---|---|---|---|
| 5,632,100 | A | 5/1997 | Hansen |
| 5,833,647 | A | 11/1998 | Edwards et al. |
| 5,985,309 | A * | 11/1999 | Edwards et al. ............. 424/426 |
| 5,985,320 | A | 11/1999 | Edwards et al. |
| 6,022,737 | A | 2/2000 | Niven et al. |
| RE37,053 | E | 2/2001 | Hanes et al. |
| 6,387,390 | B1 | 5/2002 | Deaver et al. |
| 6,423,344 | B1 | 7/2002 | Platz et al. |
| 6,586,008 | B1 | 7/2003 | Batycky et al. |
| 6,635,283 | B2 | 10/2003 | Edwards et al. |
| 6,652,873 | B2 | 11/2003 | Deaver et al. |
| 6,740,310 | B2 | 5/2004 | Edwards et al. |
| 6,848,197 | B2 * | 2/2005 | Chen et al. .................... 34/373 |
| 2003/0017113 | A1 | 1/2003 | Batycky et al. |

FOREIGN PATENT DOCUMENTS

| | | |
|---|---|---|
| WO | WO 97/39747 | 10/1997 |
| WO | WO97/39747 * | 10/1997 |
| WO | WO 01/00312 | 1/2001 |
| WO | WO 01/13892 A2 | 3/2001 |
| WO | WO 01/13893 A2 | 3/2001 |
| WO | WO 01/23821 * | 4/2001 |
| WO | WO 01/23821 A1 | 4/2001 |

OTHER PUBLICATIONS

U.S. Appl. No. 09/644,320, filed Aug. 23, 2000, Batycky et al.

Bagnolia, E. et al., "Psychrometry, Evaporative Cooling, Refrigeration, and Cryogenic Process." In Perry's Chemical Engineer's Handbook, B.B. Crawford, et al., eds., 5$^{th}$ ed. (McGraw Hill), pp. 12-1-12-13 (1994).

Broadhead, J. et al., "The Spray Drying of Pharmaceuticals," Drug Dev. And Indus. Pharm., 18(11 & 12):1169-1206 (1992).

Mintzes, "The Spray Drying of Large, Porous Particles for Aerosol Drug Delivery to the Lung," The Pennsylvania State University, University Scholars Program, pp. 1-44 Thesis for baccalaureate degree (1998).

* cited by examiner

Relationship Between Tap Density and Dew Point

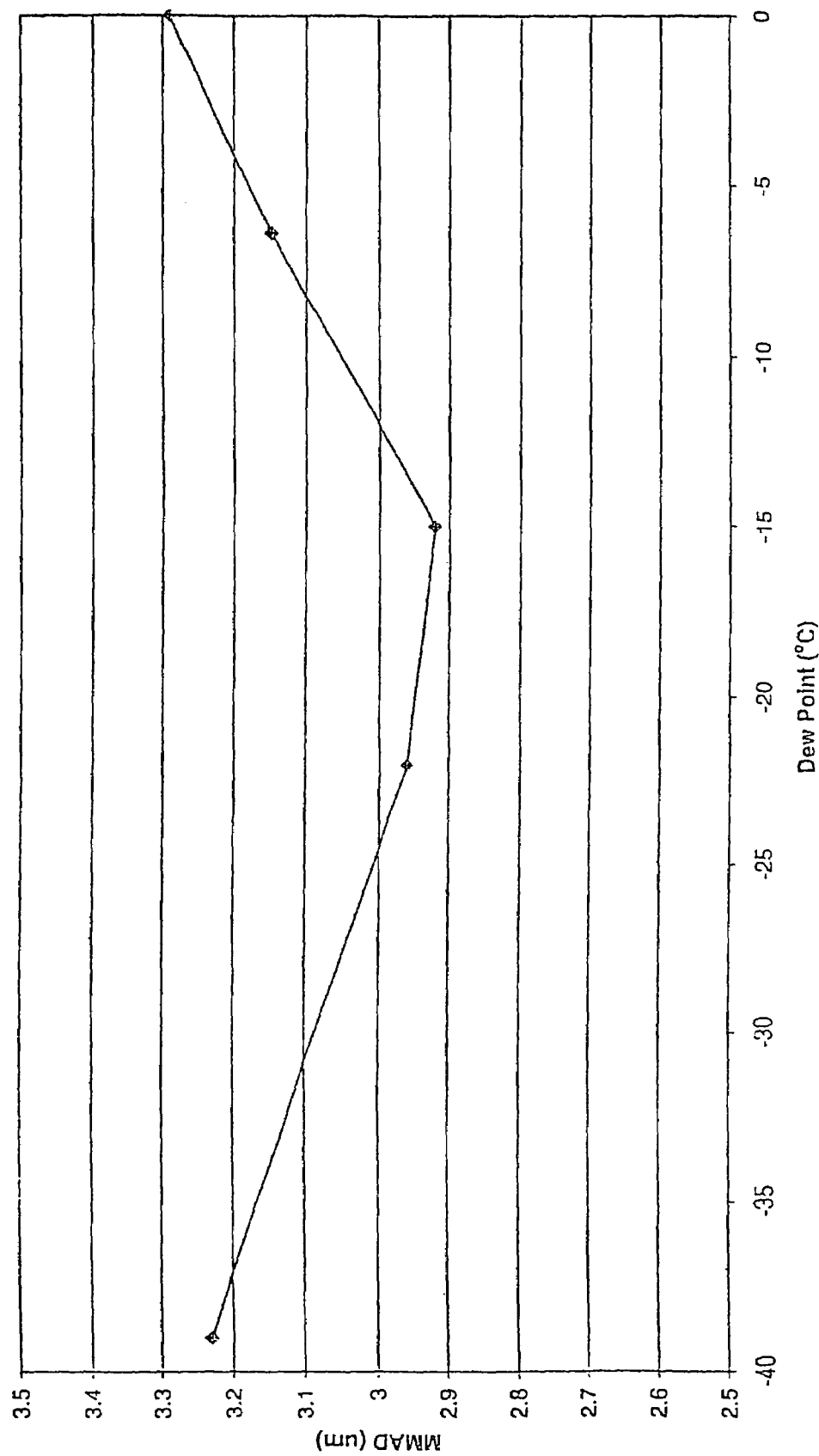

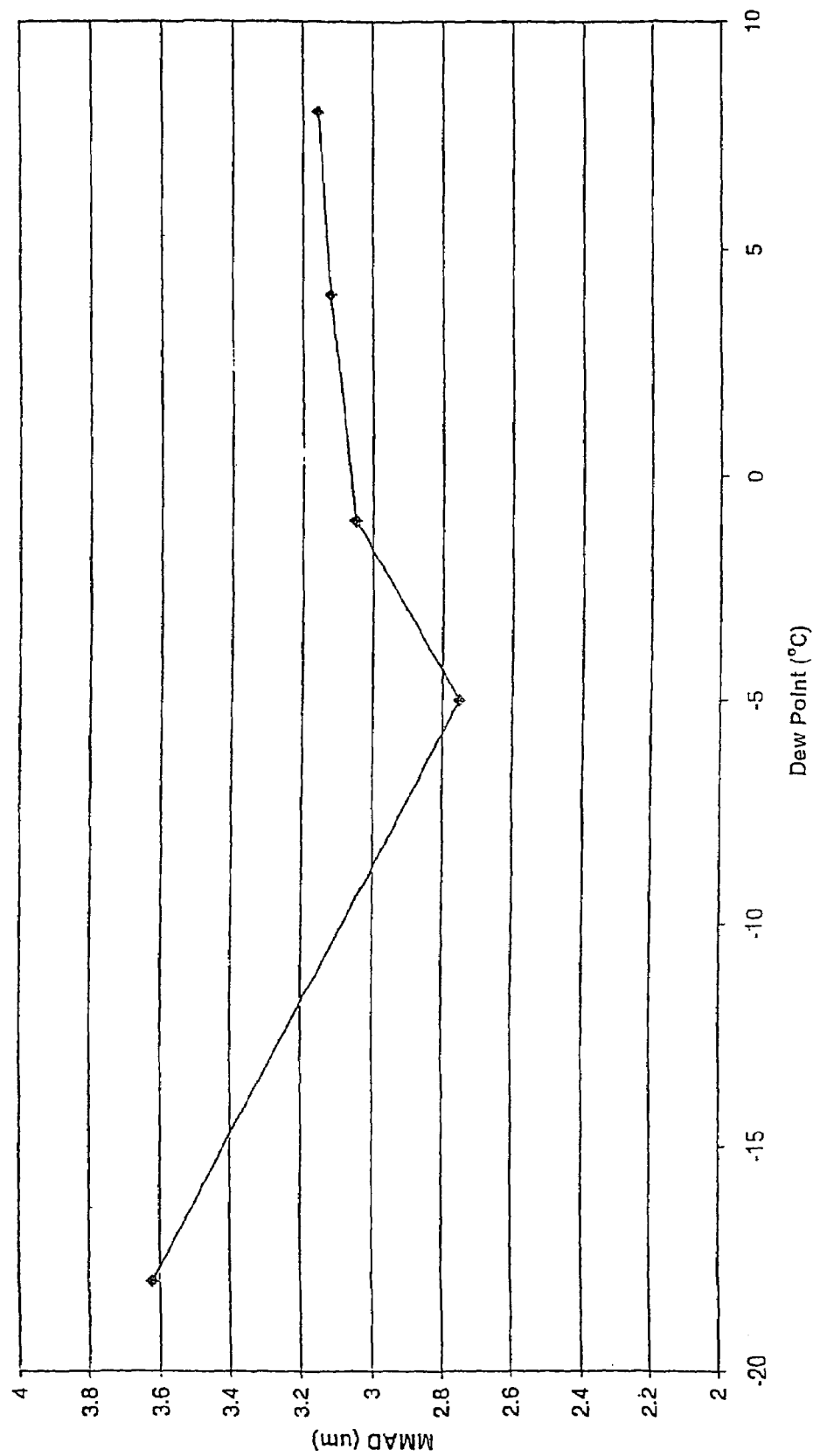

CONTROL OF PROCESS HUMIDITY TO PRODUCE LARGE, POROUS PARTICLES

RELATED APPLICATIONS

This application is a divisional of U.S. application Ser. No. 09/837,620, filed Apr. 18, 2001 now U.S. Pat. No. 6,848,197. The entire teaching of the above application is incorporated herein by reference.

BACKGROUND OF THE INVENTION

A number of techniques and devices are currently available for administering drugs to the respiratory system. Among them, metered dose inhalers (MDI) or dry powder inhalers (DPI) can be used to deliver drug formulations in the form of solid powders. Several powder properties that enhance delivery to the pulmonary system have been identified. For example, it has been found that particles which have a tap density less than 0.4 g/cm$^3$ and an aerodynamic diameter which is between about 1 and 3 microns are well suited for delivery to the alveoli or the deep lung. If delivery to the central or upper airways is desired, particles having larger aerodynamic diameters, ranging for example from about 3 to about 5 microns, are preferred. Furthermore, particles having a geometric diameter greater than about 5 microns are believed to more successfully avoid phagocytic engulfment by alveolar macrophages and clearance from the lungs.

Methods for producing particles having desired characteristics that can be tailored and optimized for delivery to selective sites of the pulmonary system, and in particular to the deep lung, continue to be needed.

SUMMARY OF THE INVENTION

The invention generally relates to producing spray dried particles having certain properties or characteristics. The properties discussed herein include tap density, volume median geometric diameter (VMGD) and mass median aerodynamic diameter (MMAD). Relationships among these properties are further discussed below. In delivering particles to the alveoli or the deep lung, particles having a low MMAD, coupled with a large VMGD are preferred.

In one embodiment, the invention relates to a method for producing spray dried particles which have targeted aerodynamic properties, for instance, tap density and/or aerodynamic diameter. The method includes atomizing a liquid feed and controlling the moisture content of a drying gas to a level selected to form particles having the targeted aerodynamic diameter or targeted tap density. The liquid droplets are contacted with the drying gas, thereby drying the liquid droplets to produce spray dried particles having the targeted aerodynamic properties.

In another embodiment, the invention relates to a method for producing particles which includes atomizing a liquid feed to produce liquid droplets and contacting the liquid droplets with a drying gas which has a dew point between about 0° C. and −40° C., thereby producing the particles. In a preferred embodiment, the particles have a tap density less than about 0.4 g/cm$^3$. In another preferred embodiment, the particles have a VMGD greater than about 5 micrometers (microns or μm) and a MMAD between about 1 μm and about 5 μm.

In other embodiments, the invention relates to methods for forming particles which have one or more targeted or desired properties, for example, a targeted or desired tap density, VMGD and/or MMAD. The methods include atomizing a liquid feed to produce liquid droplets and contacting the liquid droplets with a drying gas having a dew point which corresponds to forming particles having the targeted property or properties. In preferred embodiments, values for the tap density, VMGD and/or MMAD for a particular powder formulation are measured as a function of the dew points of the drying gas. From this correlation, a dew point corresponding to a desired or targeted value of the tap density, VMGD and/or MMAD is then selected for the particular formulation.

The invention is advantageous in producing particles which have specific characteristics. For example, in inhalation applications, particles can be tailored to enhance delivery to a specific site of the pulmonary system. The spray-dried particles produced by the methods of the invention have improved aerosolization and aerodynamic properties, low particle agglomeration and improved powder flowability. The particles are well suited for use in dry powder inhaler devices and exhibit lower deposition in the mouth, throat and in the inhaler device.

The methods of the invention are simple, economical and reproducible. By practicing the invention, production can be optimized to forming particles having desired properties. Process steps and wasted materials can be reduced and the manufacturing output of particles having specified characteristics, maximized.

Other advantages of the invention include quick drying and production ease.

BRIEF DESCRIPTION OF THE DRAWINGS

FIG. 3 is a plot showing the correlation between mass median aerodynamic diameter (MMAD) and the dew point of the process gas for spray dried particles which include DPPC (60% by weight), lactose (20% by weight) and albumin (20% by weight).

FIG. 4 is a plot showing MMAD as a function of dew point for a formulation of estradiol (90% by weight) and DPPC (10% by weight).

DETAILED DESCRIPTION OF THE INVENTION

Figure 1:
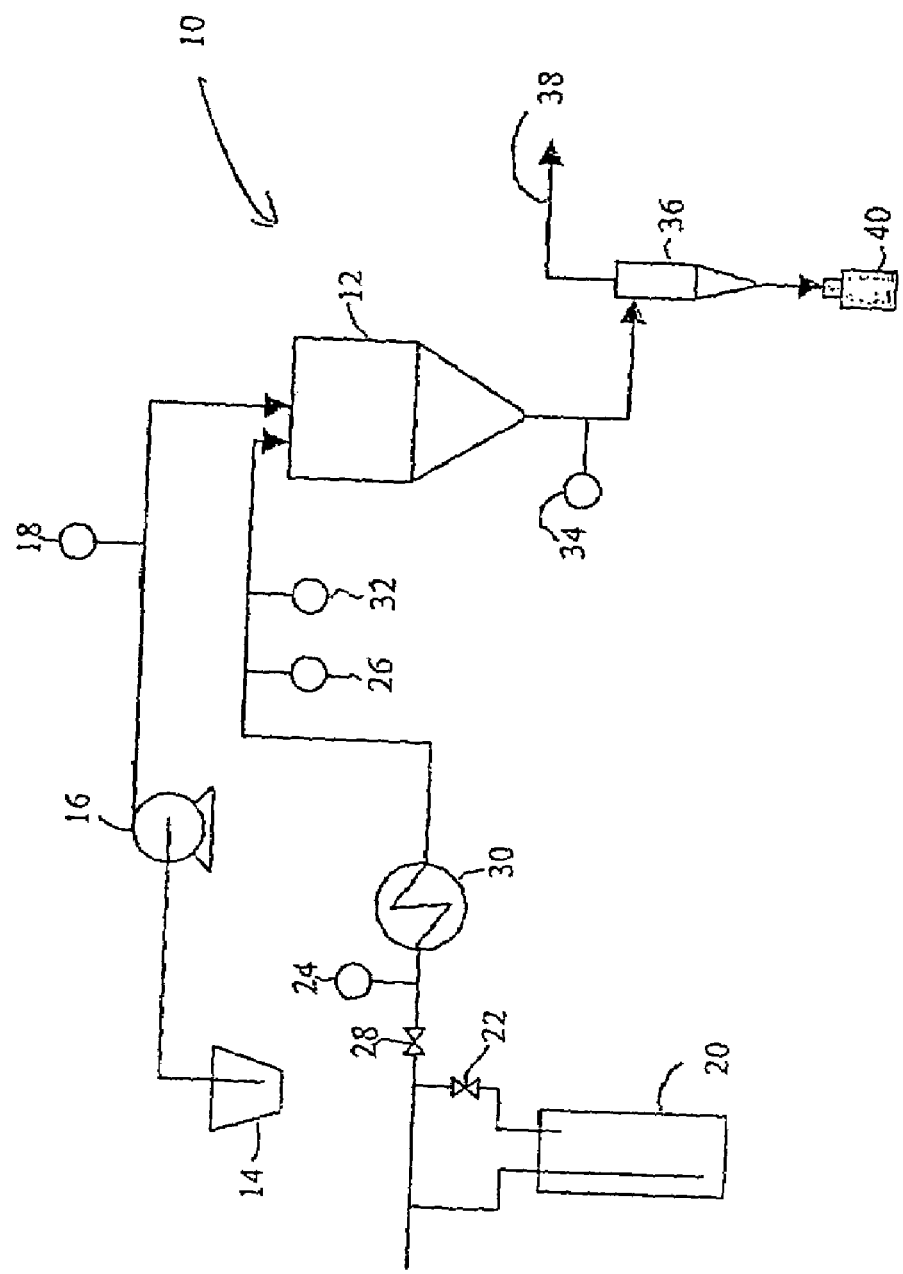
FIG. 1 is a schematic diagram of one embodiment of the apparatus which can be used to carry out the invention.

The features and other details of the invention, either as steps of the invention or as combination of parts of the invention, will now be more particularly described with reference to the accompanying drawing and pointed out in the claims. The drawing is not necessarily to scale, emphasis instead being placed upon illustrating the principles of the invention. The same numeral present in different figures represents the same item or an equivalent item. It will be understood that the particular embodiments of the invention are shown by way of illustration and not as limitations of the invention. The principle feature of this invention may be employed in various embodiments without departing from the scope of the invention.

Shown in FIG. 1 is apparatus 10, which includes spray dryer 12. Spray dryer 12 preferably employs a centrifugal atomization assembly which includes a rotating disk or wheel to break liquid feed into droplets. The rotating disk typically operates within the range from about 10,000 to about 55,000 rotations per minute (rpm). Alternatively, hydraulic pressure nozzle atomization, two fluid pneumatic atomization, sonic atomization or other atomizing techniques, as known in the art, also can be employed. In a preferred embodiment, spray dryer 12 is a Mobile Minor, EX Model manufactured by Niro, Columbia, Md. Other commercially available spray dryers from suppliers such as Niro, APV Systems, Denmark, (e.g., the APV Anhydro Model) and Swenson, Harvey, Ill., also can be employed, as can scaled-up spray dryers suitable for industrial capacity production lines. Commercially available spray dryers generally have water evaporation capacities ranging from about 1 to about 120 kg/hr. For example, a Niro Mobile MinorJ spray dryer has a water evaporation capacity of about 7 kg/hr.

Apparatus 10 also includes supply vessel 14 which holds liquid feed. Liquid feed can be supplied to vessel 14 or can be prepared in situ, from its components. A batch or a continuous mode of producing liquid feed can be employed, as known in the art. Apparatus 10 can be provided with additional supply vessels, not shown in FIG. 1.

From supply vessel 14, liquid feed is directed to spray dryer 12, for instance by means of liquid pump 16. The flow rate at which the feed liquid is being fed to spray dryer 12 can be controlled and/or monitored by flowmeter 18. In one embodiment, liquid feed is directed to spray dryer 12 at a flow rate ranging from about 10 milliliter (ml)/min to about 120 ml/min and preferably at a flow rate ranging from about 40 ml/min to about 100 ml/min. Other feed flow rates can be employed, as known in the art. For example, in larger spray dryer models, liquid feed is directed to spray dryer 12 at a flow rate ranging from about 5 to about 10 liters/min.

Liquid feed includes a solvent which can be aqueous, organic or an aqueous-organic co-solvent. Aqueous solvents include, for instance, water and buffered solutions. Examples of organic solvents include, but are not limited to, alcohols such as, for example, ethanol, methanol, propanol, isopropanol and butanols. Other organic solvents include but are not limited to perfluorocarbons, dichloromethane, chloroform, ether, ethyl acetate, methyl tert-butyl ether and others. In a preferred embodiment, the organic solvent is ethanol. If a co-solvent is employed, the amount of organic solvent can be present in the co-solvent in an amount ranging from about 10 to about 90% by volume. In a more preferred embodiment, the organic solvent is present in the co-solvent in an amount ranging from about 30 to about 85% by volume.

The liquid feed can have a neutral, acidic or alkaline pH. Optionally, a pH buffer can be added to the solvent or co-solvent or to the formed mixture. Preferably, the pH can range from about 3 to about 10.

In one embodiment of the invention, the liquid feed also includes a biologically active (bioactive) compound, for example a therapeutic, prophylactic or diagnostic agent. Bioactive compounds or agents also are referred to herein as drugs or medicaments. The amount of bioactive agent present in the liquid feed generally ranges between about 0.1% weight and about 100% weight, preferably between about 1.0% weight and about 100% weight.

Examples of biologically active agents include synthetic inorganic and organic compounds, proteins, peptides, polypeptides, DNA and RNA nucleic acid sequences having therapeutic, prophylactic or diagnostic activities. Nucleic acid sequences include genes, antisense molecules which bind to complementary DNA or RNA and inhibit transcription, and ribozymes. The agents to be incorporated can have a variety of biological activities, such as vasoactive agents, neuroactive agents, hormones, anticoagulants, immunomodulating agents, cytotoxic agents, prophylactic agents, antibiotics, antivirals, antisense, antigens, and antibodies. Compounds with a wide range of molecular weight can be used, for example, between 100 and 500,000 grams or more per mole.

The liquid feed can include a therapeutic agent for local delivery within the lung, such as agents for the treatment of asthma, chronic obstructive pulmonary disease (COPD), emphysema, or cystic fibrosis, or for systemic treatment. For example, genes for the treatment of diseases such as cystic fibrosis can be administered, as can beta agonists steroids, anticholinergics and leukotriene modifiers for asthma. Other specific therapeutic agents include, but are not limited to, human growth hormone, insulin, calcitonin, gonadotropin-releasing hormone, luteinizing hormone releasing hormone (LHRH), granulocyte colony-stimulating factor ("G-CSF"), parathyroid hormone and PTH-related peptide, somatostatin, testosterone, progesterone, estradiol, nicotine, fentanyl, norethisterone, clonidine, scopolamine, salicylate, cromolyn sodium, salmeterol, formeterol, albuterol, epinephrine, L-dopa, and diazepam, as well as medicaments that primarily target the central nervous system, kidneys, heart or other organs.

Diagnostic agents include but are not limited to imaging agents which include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include but are not limited to the gadolinium chelates currently available, such as diethylene triamine pentacetic acid (DTPA) and gadopentotate dimeglumine, as well as iron, magnesium, manganese, copper and chromium.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

Liquid feed can include additional component(s). In a preferred embodiment, liquid feed includes one or more phospholipids, such as, for example, a phosphatidylcholine, phosphatidylethanolamine, phosphatidylglycerol, phosphatidylserine, phosphatidylinositol or a combination thereof. In one embodiment, the phospholipids are endogenous to the lung. Specific examples of phospholipids are shown in Table 1. Combinations of phospholipids can also be employed.

TABLE 1

| | |
|---|---|
| Dilaurylolyphosphatidylcholine (C12;0) | DLPC |
| Dimyristoylphosphatidylcholine (C14;0) | DMPC |
| Dipalmitoylphosphatidylcholine (C16:0) | DPPC |
| Distearoylphosphatidylcholine (18:0) | DSPC |
| Dioleoylphosphatidylcholine (C18:1) | DOPC |
| Dilaurylolylphosphatidylglycerol | DLPG |
| Dimyristoylphosphatidylglycerol | DMPG |
| Dipalmitoylphosphatidylglycerol | DPPG |
| Distearoylphosphatidylglycerol | DSPG |
| Dioleoylphosphatidylglycerol | DOPG |
| Dimyristoyl phosphatidic acid | DMPA |
| Dimyristoyl phosphatidic acid | DMPA |
| Dipalmitoyl phosphatidic acid | DPPA |
| Dipalmitoyl phosphatidic acid | DPPA |
| Dimyristoyl phosphatidylethanolamine | DMPE |
| Dipalmitoyl phosphatidylethanolamine | DPPE |
| Dimyristoyl phosphatidylserine | DMPS |
| Dipalmitoyl phosphatidylserine | DPPS |
| Dipalmitoyl sphingomyelin | DPSP |
| Distearoyl sphingomyelin | DSSP |

Charged phospholipids also can be employed. Examples of charged phospholipids are described in U.S. patent application entitled "Particles for Inhalation Having Sustained Release Properties," Ser. No. 09/752,106 filed on Dec. 29, 2000, and in U.S. patent application Ser. No. 09/752,109 entitled "Particles for Inhalation Having Sustained Release Properties," filed on Dec. 29, 2000; the entire contents of both are incorporated herein by reference.

The phospholipid can be present in the liquid feed in an amount ranging from about 5 weight percent (%) to about 95 weight %. Preferably, it can be present in the particles in an amount ranging from about 20 weight % to about 80 weight %.

The phospholipids or combinations thereof can be selected to impart controlled release properties to the spray dried particles produced by the methods of the invention. Particles having controlled release properties and methods of modulating release of a biologically active agent are described in U.S. Provisional Patent Application No. 60/150,742 entitled "Modulation of Release From Dry Powder Formulations by Controlling Matrix Transition," filed on Aug. 25, 1999 and U.S. Non-Provisional patent application Ser. No. 09/644,736, filed on Aug. 23, 2000, with the title "Modulation of Release From Dry Powder Formulations." The contents of both are incorporated herein by reference in their entirety.

In another embodiment of the invention liquid feed includes a surfactant. As used herein, the term "surfactant" refers to any agent, which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

In addition to lung surfactants, such as, for example, the phospholipids discussed above, suitable surfactants include but are not limited to hexadecanol; fatty alcohols such as polyethylene glycol (PEG); polyoxyethylene-9-lauryl ether; a surface active fatty acid, such as palmitic acid or oleic acid; glycocholate; surfactin; a poloxamer; a sorbitan fatty acid ester such as sorbitan trioleate (Span 85), Tween 80 (Polyoxyethylene Sorbitan Monooleate); and tyloxapol.

The surfactant can be present in the liquid feed in an amount ranging from about 0.01 weight % to about 5 weight %. Preferably, it can be present in the particles in an amount ranging from about 0.1 weight % to about 1.0 weight %.

Methods of preparing and administering particles including surfactants, and, in particular phospholipids, are disclosed in U.S. Pat. No. 5,855,913, issued on Jan. 5, 1999 to Hanes et al. and in U.S. Pat. No. 5,985,309, issued on Nov. 16, 1999 to Edwards et al. The teachings of both are incorporated herein by reference in their entirety.

In another embodiment of the invention, the liquid feed includes an amino acid. Hydrophobic amino acids are preferred. Suitable amino acids include naturally occurring and non-naturally occurring hydrophobic amino acids. Examples of amino acids which can be employed include, but are not limited to: glycine, proline, alanine, cysteine, methionine, valine, leucine, tyrosine, isoleucine, phenylalanine, tryptophan. Preferred hydrophobic amino acids, include but not limited to, leucine, isoleucine, alanine, valine, phenylalanine, glycine and tryptophan. Amino acids which include combinations of hydrophobic amino acids can also be employed. Non-naturally occurring amino acids include, for example, beta-amino acids. Both D, L and racemic configurations of hydrophobic amino acids can be employed. Suitable hydrophobic amino acids can also include amino acid analogs. As used herein, an amino acid analog includes the D or L configuration of an amino acid having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. As used herein, aliphatic groups include straight chained, branched or cyclic C1-C8 hydrocarbons which are completely saturated, which contain one or two heteroatoms such as nitrogen, oxygen or sulfur and/or which contain one or more units of unsaturation. Aromatic groups include carbocyclic aromatic groups such as phenyl and naphthyl and heterocyclic aromatic groups such as imidazolyl, indolyl, thienyl, furanyl, pyridyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F) —O (aliphatic, substituted aliphatic, benzyl, substituted benzyl, aryl or substituted aryl group), —CN, —NO$_2$, —COOH, —NH$_2$, —NH (aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO (aliphatic group, substituted aliphatic, benzyl, substituted benzyl, aryl or substituted aryl group), —CONH$_2$, —CONH (aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(=NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents. Modifying an amino acid substituent can increase, for example, the lypophilicity or hydrophobicity of natural amino acids which are hydrophilic.

A number of the suitable amino acids, amino acid analogs and salts thereof can be obtained commercially. Others can be synthesized by methods known in the art. Synthetic techniques are described, for example, in Green and Wuts, "*Protecting Groups in Organic Synthesis*." John Wiley and Sons, Chapters 5 and 7, 1991.

Hydrophobicity is generally defined with respect to the partition of an amino acid between a nonpolar solvent and water. Hydrophobic amino acids are those acids which show a preference for the nonpolar solvent. Relative hydrophobicity of amino acids can be expressed on a hydrophobicity scale on which glycine has the value 0.5. On such a scale, amino acids which have a preference for water have values below 0.5 and those that have a preference for nonpolar solvents have a value above 0.5. As used herein, the term hydrophobic amino acid refers to an amino acid that, on the hydrophobicity scale has a value greater or equal to 0.5, in other words, has a tendency to partition in the nonpolar acid which is at least equal to that of glycine.

Combinations of hydrophobic amino acids can also be employed. Furthermore, combinations of hydrophobic and hydrophilic (preferentially partitioning in water) amino acids, where the overall combination is hydrophobic, can also be employed. Combinations of one or more amino acids and one or more phospholipids or surfactants can also be employed.

The amino acid can be present in the liquid feed in an amount from about 0 weight % to about 60 weight %. Preferably, the amino acid can be present in the liquid feed in an amount ranging from about 5 weight % to about 30 weight %.

The salt of a hydrophobic amino acid can be present in the liquid feed in an amount from about 0 weight % to about 60 weight %. Preferably, the amino acid salt is present in the liquid feed in an amount ranging from about 5 weight % to about 30 weight %. Methods of forming and delivering particles which include an amino acid are described in U.S. patent application Ser. No. 09/382,959, filed on Aug. 25, 1999, entitled "Use of Simple Amino Acids to Form Porous Particles During Spray Drying" and in U.S. patent application Ser. No. 09/644,320 filed on Aug. 23, 2000, entitled "Use of Simple Amino Acids to Form Porous Particles"; the teachings of both are incorporated herein by reference in their entirety.

In another embodiment of the invention, the liquid feed includes a carboxylate moiety and a multivalent metal salt. One or more phospholipids also can be included. Such compositions are described in U.S. Provisional Application 60/150,662, filed on Aug. 25, 1999, entitled "Formulation for Spray-Drying Large Porous Particles," and U.S. patent application Ser. No. 09/644,105 filed on Aug. 23, 2000, entitled "Formulation for Spray-Drying Large Porous Particles"; the teachings of both are incorporated herein by reference in their entirety. In a preferred embodiment, the liquid feed includes sodium citrate and calcium chloride.

Biocompatible, and preferably biodegradable polymers also can be included in the liquid feed. Particles including such polymeric materials are described in U.S. Pat. No. 5,874,064, issued on Feb. 23, 1999 to Edwards et al., the teachings of which are incorporated herein by reference in their entirety, and in U.S. Pat. No. 6,136,295, issued on Oct. 24, 2000 to Edwards et al., the entire teachings of which are incorporated herein by reference.

The liquid feed can also include a material such as, for example, dextran, polysaccharides, lactose, trehalose, cyclodextrins, proteins, peptides, polypeptides, fatty acids, inorganic compounds, phosphates.

The total concentration of solids in the liquid feed ranges from about 0.1% to about 0.5% and higher. Solids can include biologically active agent, excipient, phospholipid, surfactants, salts, buffers, metals, and other compounds.

Also directed to spray dryer 12 is a drying gas. The term "drying gas" is used herein interchangeably with the term "process gas." In a preferred embodiment the humidity level of the drying gas is controlled. Examples of gases suitable in conducting the methods of the invention include, but are not limited to, air, nitrogen, argon, carbon dioxide, helium, combinations or mixtures thereof and others. Nitrogen gas is preferred.

Drying gas which has a specified moisture level can be formed by adding moisture to a gas stream by steam injection, spraying tanks, conventional gas blending techniques and other techniques or equipment known in the art.

In a preferred embodiment of the invention, a first gas stream, from a gas source not shown in FIG. 1, is humidified by bubbling it through water, for example by passing it through pressure pot 20, after which it is combined with a second gas stream which is not humidified. The second gas stream can be obtained, for instance, directly from the gas source, without passing it through water.

External spray dryers or other equipment, including an atomizer and heater, often are present in manufacturing facilities in the pharmaceutical industry. In another embodiment of the invention, drying gas exiting from such an external spray dryer or from another apparatus including atomizer and heater, not shown in FIG. 1, is directed to the humidified drying gas, to spray dryer 12. Optionally, additional drying and/or heating of the gas exiting the external spray dryer or other equipment may be required prior to introducing it into spray dryer 12.

The flow rate of one or both streams can be regulated, as known in the art, to obtain a drying gas having a desired moisture content. For example, valve 22 as well as additional valves, not shown in FIG. 1, can be provided to control and vary gas flow rates and thus moisture levels in the drying gas. In one embodiment of the invention, the humidity of the drying gas is controlled to an accuracy of at least 1.0° C. and preferably is less than +/−0.1° C. in dew point. In FIG. 1, the dew point of the drying gas is monitored by hygrometer 24.

Dew point is the temperature to which the drying gas must be cooled, at constant pressure and constant water vapor content, in order for saturation to occur. If the dew point is below 0° C., it is often referred to as "frost point." Tables for the conversion between dew and frost points are available in meteorological applications and often can be obtained from manufacturers of hygrometers. The relationship between dew point, relative humidity, absolute humidity and dry bulb temperature is expressed in psychrometric charts, as described in Perry's Chemical Engineering Handbook, Perry, McGraw Hill.

A preferred method of measuring the dew point of the drying gas directed to spray dryer 12 includes cooling a mirror surface. An LED light source shines on the mirror surface and reflects on an optical sensor. A platinum resistance thermometer embedded beneath the mirror surface permits close monitoring of the mirror temperature. As drying gas flows, a dew layer forms onto the mirror surface. A specific example of such a hygrometer is Dew Prime™ I 2000, manufactured by Edge Tech, of Milford, Mass. The measurement range for this hygrometer is between about −50° C. to about 100° C. A suitable chiller which can be employed to cool the mirror is provided by Polyscience of Niles, Ill. as Model 1162.

Another suitable hygrometer which can be employed in carrying out the invention is Super-Dew™ provided by Shaw Moisture Meters, Ltd., Bradford, U.K. This hygrometer uses a molecular sieve adsorber with an outer conductor of 24 K gold and can measure dew points as low as −100° C.

Other means of expressing humidity levels in the drying gas, such as, for example, absolute humidity, mole fraction, partial pressure, weight of water vapor per unit volume of gas mixture and parts per million (PPM), also can be employed. How these are calculated, measured or converted into one another is known in the art.

Similarly, the invention can be practiced with solvents other than water. A common such solvent is ethanol. Other non-aqueous solvents, as known in the art, also can be employed. In such cases, instead of using a drying gas having a specified moisture content, the drying gas employed has a specified concentration of the non-aqueous solvent vapor. The solvent vapor concentration in the drying gas can be expressed, as known in the art and essentially as described above for water. Such a drying gas can be prepared essentially as described above.

The flow rate of the drying gas directed to spray dryer 12 is monitored by flowmeter 26. Valve 28 can be provided to adjust flow rate, as known in the art. In one embodiment, the flow rate of the drying gas directed to spray dryer 12 ranges from about 50 kg/hr to about 130 kg/hr, preferably from about 70 kg/hr to about 110 kg/hr. Other flow rates can be employed, as known in the art.

Drying gas is heated by heater 30. Other methods of heating the drying gas can be employed, as known in the art. The inlet temperature of the drying gas is controlled and/or monitored by thermocouple 32. Generally, drying gas is supplied to spray dryer 12 at a temperature between about 80° C. and about 200° C., preferably between about 85° C. and about 175° C.

General spray drying principles and techniques are known in the art. For example, spray drying is discussed by K. Masters In "Spray Drying Handbook," John Wiley & Sons, New York, 1984, the contents of which are incorporated herein by reference in their entirety.

During spray-drying, liquid feed directed to spray dryer 12 is atomized. The resulting droplets are contacted with hot drying gas which has a controlled moisture content, as discussed above, thereby removing solvent from the droplets and forming spray dried particles. The exit temperature of the drying gas is measured by thermocouple 34. Generally, this temperature ranges between about 35° C. and about 80° C., preferably between about 40° C. and about 70° C.

Apparatus 10 also includes cyclone 36. Cyclone 36 typically uses centrifugal action to separate the spray dried product from exhaust gases, e.g., spent drying gas and solvent vapors, which are removed from cyclone 36 via exit conduit 38. Spray dried particles are directed from cyclone 36 to powder collection jar 40. The collected spray dried particles can be stored under controlled temperature and relative humidity conditions, for example, at 22° C. and 15% RH.

In a preferred embodiment, the spray dried particles of the invention have a tap density less than about 0.4 g/cm$^3$. Particles which have a tap density of less than about 0.4 g/cm$^3$ are referred herein as "aerodynamically light particles." More preferred are particles having a tap density less than about 0.1 g/cm$^3$. Tap density can be measured by using instruments known to those skilled in the art such as but not limited to the Dual Platform Microprocessor Controlled Tap Density Tester (Vankel Technology, Cary, N.C.) or a GeoPyc™ instrument (Micrometrics Instrument Corp., Norcross, Ga. 30093). Tap density is a standard measure of the envelope mass density. Tap density can be determined using the method of USP Bulk Density and Tapped Density, United States Pharmacopeia convention, Rockville, Md., 10$^{th}$ Supplement, pgs. 4950-4951, 1999. Features which can contribute to low tap density include irregular surface texture and porous structure.

The envelope mass density of an isotropic particle is defined as the mass of the particle divided by the minimum sphere envelope volume within which it can be enclosed. In one embodiment of the invention, the particles have an envelope mass density of less than about 0.4 g/cm$^3$.

Aerodynamically light particles have a preferred size, e.g., a volume median geometric diameter (VMGD) of at least about 5 μm. In one embodiment, the VMGD is from about 5 μm to about 30 μm. In another embodiment of the invention, the particles have a VMGD ranging from about 10 μm to about 30 μm. In other embodiments, the particles have a median diameter, mass median diameter (MMD), a mass median envelope diameter (MMED) or a mass median geometric diameter (MMGD) of at least 5 μm, for example from about 5 μm to about 30 μm.

The diameter of the spray-dried particles, for example, the VMGD, can be measured using an electrical zone sensing instrument such as a Multisizer IIe, (Coulter Electronic, Luton, Beds, England), or a laser diffraction instrument (for example Helos, manufactured by Sympatec, Princeton, N.J.). Other instruments for measuring particle diameter are well known in the art. The diameter of particles in a sample will range depending upon factors such as particle composition and methods of synthesis. The distribution of size of particles in a sample can be selected to permit optimal deposition to targeted sites within the respiratory tract.

Aerodynamically light particles preferably have "mass median aerodynamic diameter" (MMAD), also referred to herein as "aerodynamic diameter," between about 1 μm and about 5 μm. In another embodiment of the invention, the MMAD is between about 1 μm and about 3 μm. In a further embodiment, the MMAD is between about 3 μm and about 5 μm.

Experimentally, aerodynamic diameter can be determined by employing a gravitational settling method, whereby the time for an ensemble of particles to settle a certain distance is used to infer directly the aerodynamic diameter of the particles. An indirect method for measuring the mass median aerodynamic diameter (MMAD) is the multi-stage liquid impinger (MSLI). Alternative instruments which can be employed to determine aerodynamic diameters include those known under the name of Aerosizerj (TSI, Inc., Amherst, Mass.) or under the name of Anderson Cascade Impactor (Anderson Inst., Sunyra, Ga.).

The aerodynamic diameter, $d_{aer}$, can be calculated from the equation:

$$d_{aer} = d_g \sqrt{\rho_{tap}}$$

where $d_g$ is the geometric diameter, for example the MMGD, and $\rho_{tap}$ is the powder tap density.

Particles which have a tap density less than about 0.4 g/cm$^3$, median diameters of at least about 5 μm, and an aerodynamic diameter of between about 1 μm and about 5 μm, preferably between about 1 μm and about 3 μm, are more capable of escaping inertial and gravitational deposition in the oropharyngeal region, and are targeted to the airways, particularly the deep lung. The use of larger, more porous particles is advantageous since they are able to aerosolize more efficiently than smaller, denser aerosol particles such as those currently used for inhalation therapies.

In another embodiment of the invention, the particles have an envelope mass density, also referred to herein as "mass density" of less than about 0.4 g/cm$^3$. Particles also having a mean diameter of between about 5 μm and about 30 μm are preferred. Mass density and the relationship between mass density, mean diameter and aerodynamic diameter are discussed in U.S. application Ser. No. 08/655,570, filed on May 24, 1996, which is incorporated herein by reference in its entirety. In a preferred embodiment, the aerodynamic diameter of particles having a mass density less than about 0.4 g/cm$^3$ and a mean diameter of between about 5 μm and about 30 μm mass mean aerodynamic diameter is between about 1 μm and about 5 μm.

In comparison to smaller, relatively denser particles the larger aerodynamically light particles, preferably having a median diameter of at least about 5 μm, also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond about 3 μm. Kawaguchi, H., et al., *Biomaterials*, 7:61-66 (1986); Krenis, L. J. and Strauss, B., *Proc. Soc. Exp. Med.*, 107:748-750 (1961); and Rudt, S. and Muller, R. H., *J. Contr. Rel.*, 22:263-272 (1992). For particles of statistically isotropic shape, such as spheres with rough surfaces, the particle envelope volume is approximately equivalent to the volume of cytosolic space required within a macrophage for complete particle phagocytosis.

The particles may be fabricated with the appropriate material, surface roughness, diameter and tap density for localized delivery to selected regions of the respiratory tract such as the deep lung or upper or central airways. For example, higher density or larger particles may be used for upper airway delivery, or a mixture of varying sized particles in a sample, provided with the same or different therapeutic agent may be administered to target different regions of the lung in one administration. Particles having an aerodynamic diameter ranging from about 3 to about 5 μm are preferred for delivery to the central and upper airways. Particles having and aerodynamic diameter ranging from about 1 to about 3 μm are preferred for delivery to the deep lung.

Inertial impaction and gravitational settling of aerosols are predominant deposition mechanisms in the airways and acini of the lungs during normal breathing conditions. Edwards, D. A., *J. Aerosol Sci.*, 26:293-317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 μm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," In *Topics in Pharmaceutical Sciences*, (1991) (eds. D. J. A. Crommelin and K. K. Midha), pp. 95-117, Stuttgart: Medpharm Scientific Publishers, 1992)), by the formula:

$$d_{aer} = d\sqrt{\rho}$$

where the envelope mass ρ is in units of g/cm³. Maximal deposition of monodispersed aerosol particles in the alveolar region of the human lung (~60%) occurs for an aerodynamic diameter of approximately $d_{aer}$=3 μm. Heyder, J. et al., *J. Aerosol Sci.*, 17:811-825 (1986). Due to their small envelope mass density, the actual diameter d of aerodynamically light particles comprising a monodisperse inhaled powder that will exhibit maximum deep-lung deposition is:

$$d = 3/\sqrt{\rho} \, \mu m \text{ (where } \rho < 1 \text{ g/cm}^3\text{)};$$

where d is always greater than 3 μm. For example, aerodynamically light particles that display an envelope mass density, ρ=0.1 g/cm³, will exhibit a maximum deposition for particles having envelope diameters as large as 9.5 μm. The increased particle size diminishes interparticle adhesion forces. Visser, J., *Powder Technology*, 58:1-10. Thus, large particle size increases efficiency of aerosolization to the deep lung for particles of low envelope mass density, in addition to contributing to lower phagocytic losses.

The aerodynamic diameter can be calculated to provide for maximum deposition within the lungs. Previously this was achieved by the use of very small particles of less than about five microns in diameter, preferably between about one and about three microns, which are then subject to phagocytosis. Selection of particles which have a larger diameter, but which are sufficiently light (hence the characterization "aerodynamically light"), results in an equivalent delivery to the lungs, but the larger size particles are not phagocytosed.

The methods of the invention include controlling the properties of the spray dried particles by manipulating the moisture content of the drying gas. For example, it has been found that the moisture present in the drying gas can be optimized to produce particles which combine large geometrical dimensions, e.g., VMGD, and low tap density and which have aerodynamic properties that promote delivery to the alveoli or the deep lung. On the other hand, using a drying gas having too high or too low a moisture content, when compared to the optimized humidity level, results in an increase in tap density, and MMAD and a decrease in VMGD. The latter particles can be tailored, for example, for preferential delivery to the central airways.

For a given formulation, the relationship between the aerodynamic properties of the particles and the moisture content of the drying gas, expressed, for instance, in terms of the set or established dew point, can be determined experimentally as follows. Particles can be spray dried employing a process gas having specified dew points. For each dew point value, properties of the spray dried particles, e.g., tap density, VMGD, MMAD, can be measured. A correlation between the dew point and the tap density, VMGD or MMAD over the dew point range employed can be generated. The correlation can then be employed to select a dew point which results in the formation of particles having desired properties.

In one embodiment of the invention, spray dried particles are formed by employing a drying gas having a dew point ranging between about 0° C. and about −40° C. For example, for enhanced delivery to the deep lung, a dew point of −40° C. is preferred in spray drying particles having a 50/50 weight percent of DPPC/human growth hormone or hGH. A dew point of about −20° C. is preferred for a formulation which includes 38/38/16/8 weight percent of DSPC/DPPC/leucine/albuterol sulfate. Formulations of 74.5/24.0/1.5 weight percent of DSPC/leucine/salmeterol can be spray dried using a drying gas with a dew point of about −20° C. A dew point of −30° C. is preferred in spray drying formulations which include a monoclonal antibody such as a humanized monoclonal antibody IgG1 and DPPC (60/40 monoclonal antibody/DPPC by weight percent).

Particles produced by the methods of the invention and which include a medicament, for example one or more of the bioactive agents described above, can be administered to the respiratory tract of a patient in need of treatment, prophylaxis or diagnosis. Administration of particles to the respiratory system can be by means such as known in the art. For example, particles are delivered from an inhalation device. In a preferred embodiment, particles are administered via a dry powder inhaler (DPI). Metered-dose-inhalers (MDI), or instillation techniques also can be employed.

Various suitable devices and methods of inhalation which can be used to administer particles to a patient's respiratory tract are known in the art. For example, suitable inhalers are described in U.S. Pat. No. 4,069,819, issued Aug. 5, 1976 to Valentini, et al., U.S. Pat. No. 4,995,385 issued Feb. 26, 1991 to Valentini, et al., and U.S. Pat. No. 5,997,848, issued Dec. 7, 1999 to Patton, et al. Other examples of suitable inhalers include, but are not limited to, the Spinhaler7 (Fisons, Loughborough, U.K.), Rotahaler7 (Glaxo-Wellcome, Research Triangle Technology Park, North Carolina), FlowCaps7 (Hovione, Loures, Portugal), Inhalator7 (Boehringer-Ingelheim, Germany), and the Aerolizer7 (Novartis, Switzerland), the Diskhaler7 (Glaxo-Wellcome, RTP, NC) and others, such as known to those skilled in the art.

Preferably, particles administered to the respiratory tract travel through the upper airways (oropharynx and larynx), the lower airways which include the trachea followed by bifurcations into the bronchi and bronchioli and through the terminal bronchioli which in turn divide into respiratory bronchioli leading then to the ultimate respiratory zone, the alveoli or the deep lung. In a preferred embodiment of the invention, most of the mass of particles deposits in the deep lung. In another embodiment of the invention, delivery is primarily to the central airways. Delivery to the upper airways can also be obtained.

In one embodiment of the invention, delivery to the pulmonary system of particles is in a single, breath-actuated step, as described in U.S. Non-Provisional patent application, "High Efficient Delivery of a Large Therapeutic Mass Aerosol," application Ser. No. 09/591,307, filed Jun. 9, 2000, which is incorporated herein by reference in its entirety. In another embodiment of the invention, at least 50% of the mass of the particles stored in the inhaler receptacle is delivered to a subject's respiratory system in a single, breath-activated step. In a further embodiment, at least 5 milligrams and preferably at least 10 milligrams of a medicament is delivered by administering, in a single breath, to a subject's respiratory tract particles enclosed in the receptacle. Amounts as high as 15, 20, 25, 30, 35, 40 and 50 milligrams can be delivered.

As used herein, the term "effective amount" means the amount needed to achieve the desired therapeutic or diagnostic effect or efficacy. The actual effective amounts of drug can vary according to the specific drug or combination thereof being utilized, the particular composition formulated, the mode of administration, and the age, weight, condition of the patient, and severity of the symptoms or condition being treated. Dosages for a particular patient can be determined by one of ordinary skill in the art using conventional considerations, (e.g. by means of an appropriate, conventional pharmacological protocol). In one example, effective amounts of albuterol sulfate range from about 100 micrograms (μg) to about 1.0 milligram (mg).

Aerosol dosage, formulations and delivery systems also may be selected for a particular therapeutic application, as described, for example, In Gonda, I., "Aerosols for delivery of therapeutic and diagnostic agents to the respiratory tract," In *Critical Reviews in Therapeutic Drug Carrier Systems*, 6:273-313, 1990; and In Moren, "Aerosol dosage forms and formulations," In *Aerosols in Medicine. Principles, Diagnosis and Therapy*, Moren, et al., Eds, Esevier, Amsterdam, 1985.

The particles of the invention can be employed in compositions suitable for drug delivery to the pulmonary system. For example, such compositions can include the particles and a pharmaceutically acceptable carrier for administration to a patient, preferably for administration via inhalation. The particles may be administered alone or in any appropriate pharmaceutically acceptable carrier, such as a liquid, for example saline, or a powder, for administration to the respiratory system. They can be co-delivered with larger carrier particles, not including a therapeutic agent, the latter possessing mass median diameters for example in the range between about 50 μm and about 100 μm.

The present invention will be further understood by reference to the following non-limiting examples.

EXEMPLIFICATION

The liquid pump used in these experiments was a Masterflex, Model 2000 from Cole-Parmer Instrument Company. The liquid mass flowmeter was Promass 64, while the gas mass flowmeter was a Promass F. Both were manufactured by Endress and Hauser, Switzerland. The Hygrometer/Chiller used was a Dew Prime I, Model 2000 (Edge Tech, Milford, Mass.)/Model 1162 (Polyscience, Niles, Ill.). The spray dryer was a Mobile Minor, EX Model, from Niro Inc., Columbia Md. The atomizer used was SL24-50/M-02/B with straight vanes, also from Niro, Columbia, Md. The collection jar was a 1L glass jar (Niro, Columbia, Md.).

EXAMPLE 1

A formulation including 60/20/20 percent by weight of DPPC, lactose and albumin was prepared as follows.

DPPC (1,2-Dipalmitoyl-sn-Glycero-3-phosphocholine), obtained from Avanti Polar Labs, Alabaster, Ala. and the albumin, bovine, fraction V, obtained from Sigma, St. Louis, Mo., were removed from cold storage and allowed to warm to room temperature, typically for at least about 20 minutes. 600 mg DPPC was dissolved in 850 ml ethyl alcohol, 200 proof, USP. 200 mg B-lactose anhydrate, USP grade, from Spectrum Laboratories, Laguna Hills, Calif., was dissolved in 150 ml USP sterile water. Once the solution became clear, 200 mg albumin were dissolved in the above aqueous solution. The pH of the aqueous solution, measured by a pH/ion analyzer, model # 355, from Corning Inc., Corning, N.Y., was adjusted to 8.1±0.1 using 1.0N sodium hydroxide solution.

The aqueous phase was slowly poured into the ethanol phase with continued stirring until solution became clear. 850 ml Ethyl alcohol, 200 proof, USP was placed into the 1 L glass bottle with stir bar. 150 ml of USP sterile water was mixed with the ethanol phase by slowly pouring water into ethanol phase, with stirring until the solution became clear.

The spray drying was carried out using a liquid feed rate of 48 ml/minute and a process gas rate of 88 kg/hour. The pressure to the rotary atomizer was adjusted to obtain a wheel speed of about 18800 rotations per minute (rpm).

The other spray drying parameters are shown in Table 2 and the dew points employed are shown in Table 2. Also shown in Table 2 are the tap densities, VMGD and MMAD of the spray dried particles.

TABLE 2

| Run # | T Inlet (° C.) | T Outlet (° C.) | Dew Point (° C.) | Tap ρ (g/cm$^3$) | VMGD (μm) | MMAD (μm) |
|---|---|---|---|---|---|---|
| 1 | 110 | 58 | −22 | 0.104 | 7.61 | 2.96 |
| 2 | 110 | 59 | −15 | 0.124 | 7.47 | 2.92 |
| 3 | 110 | 60 | −6.4 | 0.24 | 6.4 | 3.15 |
| 4 | 110 | 60 | 0 | 0.28 | 6.15 | 3.29 |
| 5 | 110 | 58 | −39 | 0.169 | 7.2 | 3.23 |

Figure 2:
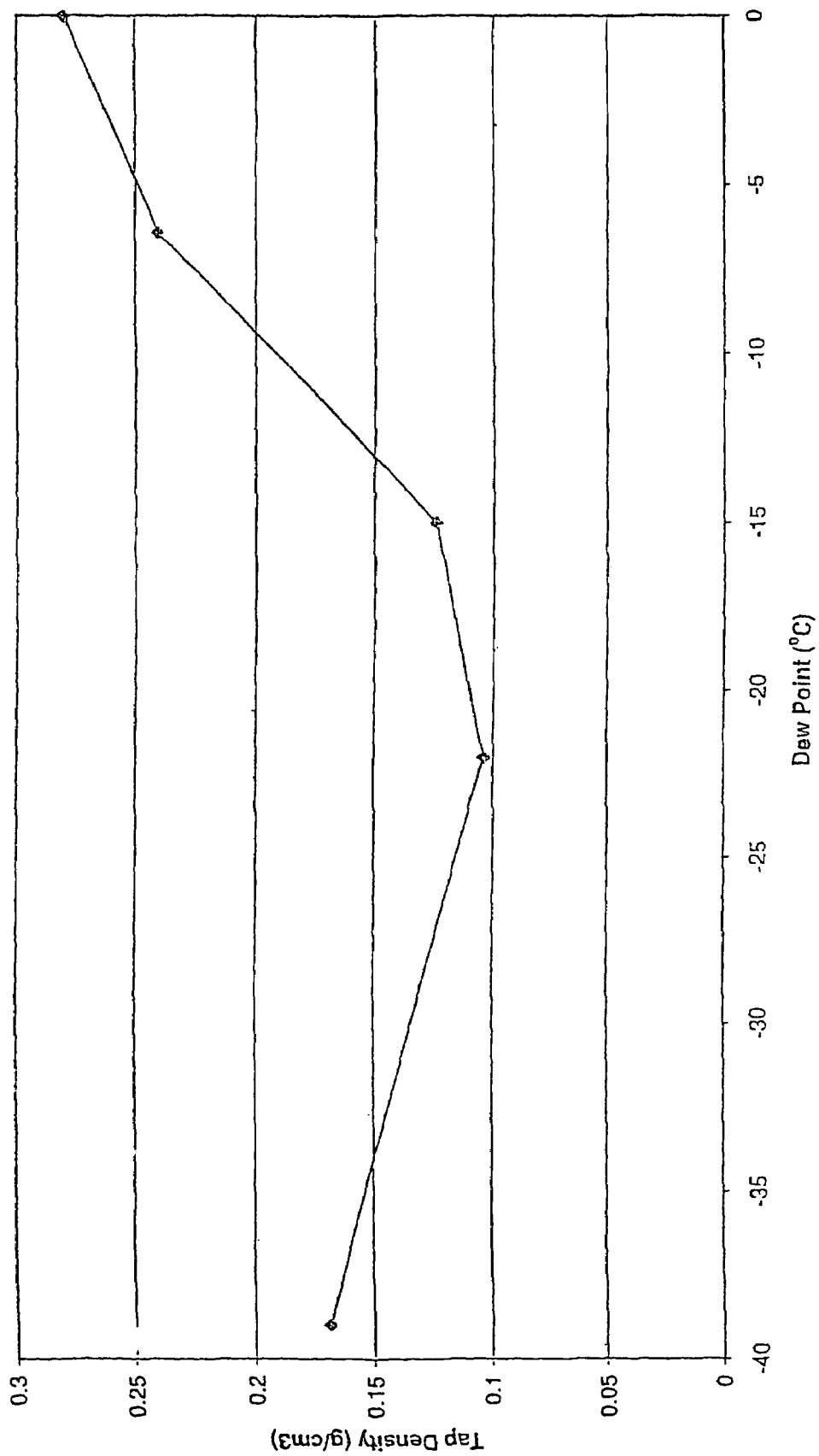
FIG. 2 is a plot showing the correlation between dew point of the process gas and the tap density of spray dried particles which include DPPC (60% by weight), lactose (20% by weight) and albumin (20% by weight).

A plot showing the correlation or relationship between dew point (in degrees C.) of the process gas and the tap density of the resulting spray dried particles is shown in FIG. 2. FIG. 3 is a plot showing the relationship between MMAD and the dew point (in degrees C.) of the process gas.

As can be seen from Table 2 and FIGS. 2 and 3, for this formulation, the optimal dew point range for producing particles which have minimized tap density, largest VMGD and lowest MMAD can be produced by employing a drying gas which has a dew point ranging between about −15° C. and about −22° C. Dew point values outside this range can be selected to form particles which have higher tap densities and higher MMAD.

EXAMPLE 2

A formulation including 10 weight % DPPC, obtained from Avanti Polar Labs Alabaster, Ala. and 90 weight % estradiol, obtained from Spectrum Quality Products, New Brunswick, N.J. was spray dried using a 70/30 volume/volume ethanol/water solvent. The solid concentration was 3 g/l. The process gas used was air. Spray drying parameters used and the MMAD of the spray dried particles formed employing process gas at different dew point values are shown in Table 3 and FIG. 4. As seen from Table 3 and FIG. 4, the MMAD was minimized when process air had a dew point of about −5° C. Higher or lower dew points can be selected to form particles having the 90/10 estradiol/DPPC formulation and larger MMAD values.

TABLE 3

| Run | $T_{inlet}$ (° C.) | $T_{outlet}$ (° C.) | Atomization (rpm) | Process gas (kg/hr) | Liquid Feed (ml/min) | Dew point (° C.) | MMAD (μm) |
|---|---|---|---|---|---|---|---|
| 1 | 110 | 58 | 14600 | 85 | 40 | −1 | 3.05 |
| 2 | 110 | 58 | 14600 | 85 | 40 | −5 | 2.75 |
| 3 | 110 | 60 | 14600 | 85 | 40 | 4 | 3.12 |
| 4 | 110 | 59 | 14600 | 85 | 40 | −18 | 3.62 |
| 5 | 110 | 59 | 14600 | 85 | 40 | 8 | 3.16 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of producing spray dried particles suitable for inhalation comprising:
    a) correlating a dew point value of a drying gas with the resulting tap density, median geometric diameter, and median aerodynamic diameter of the spray dried particles formed by contacting a sprayed liquid feed with the drying gas over a range of drying gas dew point values;
    b) selecting a dew point value of a drying gas from the range of dew point values of step (a) that corresponds to a targeted median geometric diameter, a targeted median aerodynamic diameter and a targeted tap density of spray-dried particles;
    c) generating a drying gas having said selected dew point; and
    d) contacting the sprayed liquid feed with the drying gas having said selected dew point thereby producing particles having the targeted median aerodynamic diameter, targeted tap density and targeted median geometric diameter, wherein said particles are suitable for inhalation.

2. The method of claim 1, wherein the aerodynamic diameter is less than about 3 microns.

3. The method of claim 1, wherein the tap density is less than about 0.4 g/cm$^3$.

4. The method of claim 3, wherein the tap density is less than about 0.1 g/cm$^3$.

5. The method of claim 1, wherein the drying gas has a temperature of between about 80° C. and about 200° C. at the inlet.

6. The method of claim 1, wherein the drying gas has temperature between about 350° C. and about 80° C. at the outlet.

7. The method of claim 1 further comprising separating the spray dried particles from waste drying gas.

8. The method of claim 1 further comprising collecting the spray dried particles.

9. The method of claim 1, wherein the liquid feed includes a solvent selected from the group consisting of an organic solvent, an aqueous solvent or any combination thereof.

10. The method of claim 1, wherein the spray dried particles comprise a bioactive agent.

11. The method of claim 1, wherein the spray dried particles comprise a phospholipid.

12. A method of producing spray dried particles formed by contacting a sprayed liquid feed with a drying gas comprising the steps of:
    a) correlating a dew point of a drying gas to a level selected to form spray dried particles having a median aerodynamic diameter of less than about 5 μm, a tap density of less than about 0.4 g/cm$^3$ and a geometric diameter of less than about 30 μm of particles;
    b) generating a nitrogen drying gas having the correlated dew point of step (a);and
    c) contacting the sprayed liquid feed with the nitrogen drying gas having said selected dew point thereby producing particles having a median aerodynamic diameter of less than about 5 μm, a tap density of less than about 0.4 g/cm$^3$ and a geometric diameter of less than about 30 μm, wherein said particles are suitable for inhalation.

13. The method of claim 12 further comprising the step of maintaining the temperature of the dew point of the drying gas to an accuracy of at least 1° C.

* * * * *